United States Patent [19]
Etchells, III et al.

[11] Patent Number: 5,215,926
[45] Date of Patent: Jun. 1, 1993

[54] PROCEDURE FOR DESIGNING EFFICIENT AFFINITY CELL SEPARATION PROCESSES

[75] Inventors: Arthur W. Etchells, III, Philadelphia, Pa.; Dale R. Peterson, Wilmington, Del.

[73] Assignee: CellPro, Inc., Bothell, Wash.

[21] Appl. No.: 630,337

[22] Filed: Dec. 17, 1990

Related U.S. Application Data

[63] Continuation of Ser. No. 202,034, Jun. 3, 1988, abandoned.

[51] Int. Cl.$^5$ .......................................... G01N 33/566
[52] U.S. Cl. .................................. 436/501; 436/518; 436/531; 436/824
[58] Field of Search ............... 436/501, 518, 536, 538, 436/541, 52, 824, 531; 435/2, 7.1, 7.2; 604/4-6; 210/656, 660, 677, 678, 670, 695; 530/413, 415-417

[56] References Cited

U.S. PATENT DOCUMENTS

| | | | |
|---|---|---|---|
| 3,843,324 | 10/1974 | Edelman et al. | 23/230 B |
| 3,970,518 | 7/1976 | Giaever | 195/1.5 |
| 4,035,316 | 7/1977 | Yen et al. | 260/2.5 B |
| 4,230,635 | 10/1980 | Senyei et al. | 424/12 |
| 4,363,634 | 12/1982 | Schall, Jr. | 23/230 B |
| 4,619,904 | 10/1986 | Giaver et al. | 436/518 |

OTHER PUBLICATIONS

Duszyk et al., "Hydrodynamics of Interaction of Particles with Surfaces", Progress In Surface Science, vol. 15, (1984), pp. 369-399.
Kemshead et al., "Monclonal Antibodies . . . ", Advances in Neuroblastoma Research, (1985) pp. 413-423.
Fong "Solid Phase Fractionation of Lymphoid Cells on Ligand-Coated Plastic Plates" Cell Separation Methods and Selected Applications (New York, Academic Press, 1983), pp. 203-219.
Jasiewicz, M. L., et al., "Selective Retrieval of Biotin-Labeled Cells Using Immobilized Avidin", *Experimental Cell Research* 100:213-217, 1976.
Wigzell and Anderson, J. Exp. Med. 129:23-36 (1977).
Rutishauser et al., Proc. Natl. Acad. Sci., 70:3894-3898 (1973).
Mage et al., J. Immunol. Meth. 15:47-56 (1977).
Wysocki and Sato, Proc. Natl. Acad. Sci., 75:2844-2848 (1978).
Wigzell, Scandl. J. Immunol., 5:23-30 (1976).
Antoine et al., Immunochem, 15:443-452 (1987).
Edelman and Rutishauser, Meth. Enzymol., 34:195-225 (1974).
Treleaven et al, Lancet 1:70-73 (1984).
Berenson et al., J. Immunol Methods, 91:11-19 (1986).
Gaudernack et al., J. Immunol Methods, 90:179-187 (1986).
Hertz et al., Biotechnology and Bioengineering, 27:603-612 (1985).
Berenson et al., J. Cell Biochem., 10D:239 (1986).
Vartdal et al., J. Cell Biochem., Sup., 10D:252 (1986).

*Primary Examiner*—Michael G. Wityshyn
*Assistant Examiner*—William H. Beisner
*Attorney, Agent, or Firm*—Seed and Berry

[57] ABSTRACT

Processes using affinity cell separation are used to increase the yield and purities of target cells by increasing the cell:affinity surface contact rate, limiting the shear force on the attaching cells and/or using an appropriate affinity surface area.

31 Claims, 1 Drawing Sheet

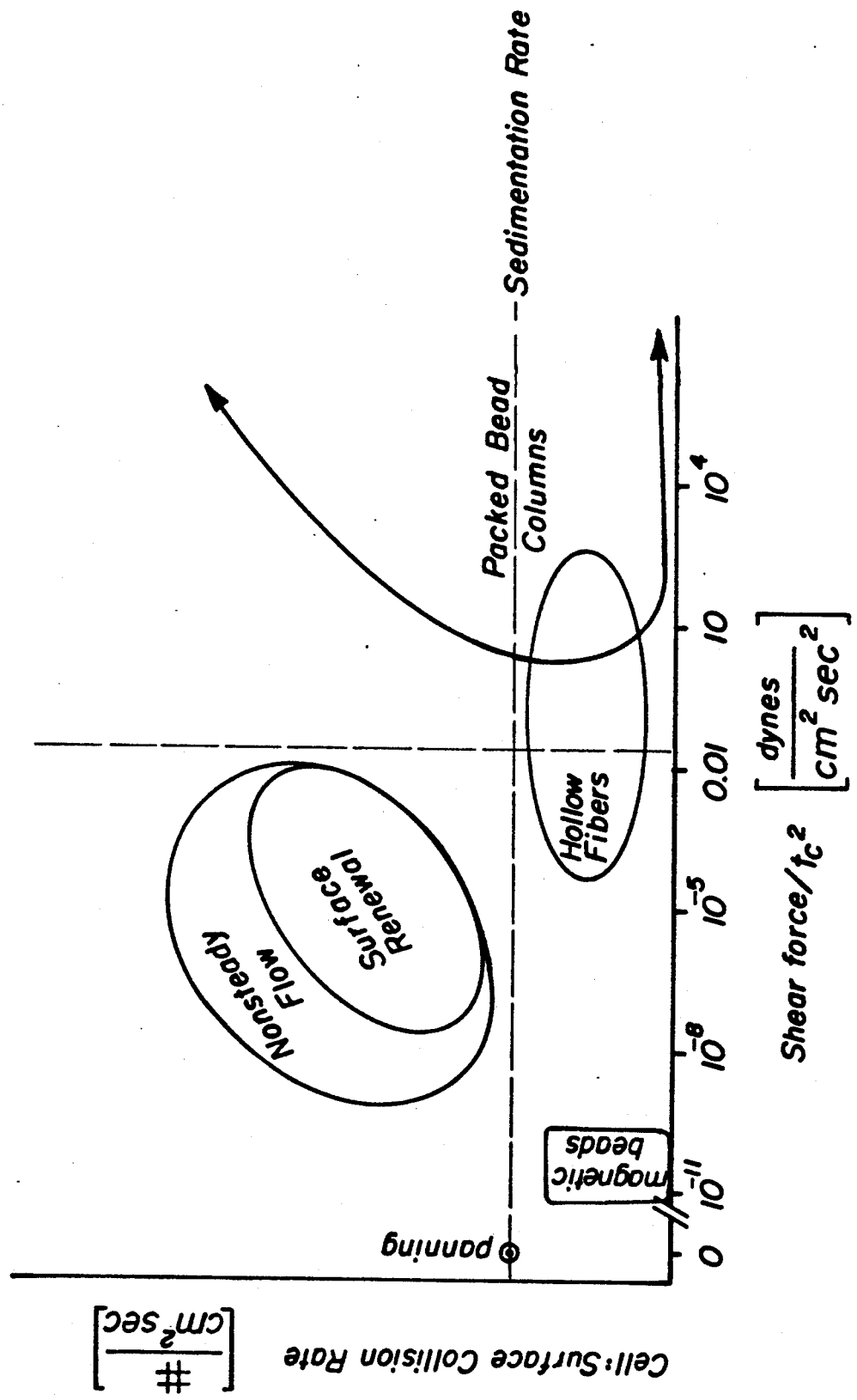

PROCEDURE FOR DESIGNING EFFICIENT AFFINITY CELL SEPARATION PROCESSES

CROSS-REFERENCE TO RELATED APPLICATION

This application is a continuation of U.S. application Ser. No. 07/202,034 filed Jun. 3, 1988, now abandoned.

FIELD OF THE INVENTION

The invention relates to a method of designing affinity selection processes for separating specific biological cells from a cell mixture.

BACKGROUND OF THE INVENTION

Affinity separation of cells refers to known process techniques where a particular subset of a mixture or population of biological cells are bound to support surfaces by means of ligands with specific affinity to molecules or structures on the cell membranes of the subset. Cells which lack the membrane molecules or structures are not bound to the support surface and can be removed from the population to effect a separation of these cells from the bound cells or vice versa.

Affinity separation processes are commonly used either to eliminate a subset from the mixture of interest (depletion) or to prepare a specific subset of interest from a mixture (positive selection). The depletion process is much simpler because the bound cells are simply discarded leaving the desired cells behind. Positive selection is much more difficult both because the desired cells are bound to the support and must be removed without damaging them and because a certain proportion of the undesirable cells can and do bind nonspecifically to the affinity surface and contaminate the collected cells.

Cell separation techniques have important potential application in cancer therapies, autoimmune disease therapies, and improved diagnostics. For example, cell affinity devices can be used in extracorporeal therapies that may involve the selective isolation, augmentation, and reintroduction to the host of a specific subset population of cells.

Cell affinity techniques have been used widely since Wigzell's description of such a process in 1969 (Wigzell and Andersson *J. Exp. Med.* 129:23–36, 1969). Cells have been separated using antibodies immobilized to beads (Wigzell and Andersson *J. Exp. Med.* 129:23–36, 1969), to fibers (Rutishauser et al. *Proc. Natl. Acad. Sci.* 70, 1973), to petri dishes (Mage et al. *J. Immunol. Meth.* 15, 1977), and to liquid droplets (U.S. Pat. No. 4,619,904). The separation process basically involves effecting contact between cell mixtures and a ligand-coated support, allowing the cells to bind, and then washing away nonadherent cells.

During the 1970's there were several reports of cell affinity separation techniques for a variety of cells, supports, and ligands (Wysocki and Sato *Proc. Natl. Acad. Sci.* 75:2844–2848, 1978; Wigzell *Scand. J. Immunol.* 5:23–30, 1976; Antoine et al. *Immunochem.* 15, 1987; Edelman and Rutishauser *Meth. Enzymol.* 34:195–225, 1974). Several patents have issued describing a variety of techniques and devices for affinity cell separations (U.S. Pat. Nos. 4,035,316; 3,970,518; 3,843,324; 4,230,685; 4,363,634). With the exception of panning and certain procedures involving the use of magnetic particles, the techniques have proven difficult to reproduce. Moreover, the many attempts to scale-up these procedures have been very disappointing.

Affinity cell depletion techniques have found some important applications. Researchers prepare specific cell subpopulations for study by systematically depleting a mixture of various subpopulations of cells. For example, Treleavan et al. (Treleaven et al. *Lancet* 1:70–73, 1984) have demonstrated that the concentration of neuroblastoma cells in a bone marrow preparation can be reduced by a factor of about $10^6$ using multiple depletions with antibody-coated magnetic beads.

Two examples of positive selection techniques are those described by Berenson et al. (*J. Immunol. Methods* 91:11–19, 1986) and by Gaudernack et al. (*J. Immunol. Methods* 90:179–187, 1986). Berenson et al. bind biotinylated antibodies to target cells and pass them through a column packed with avidin-coated beads, thereby recovering 64% of a population of human bone marrow cells at a final concentration of 73% when the initial concentration was 7%. Gaudernack et al. use antibody-coated magnetic beads to collect a certain subset of T cells. The initial concentration was 30%, and the positively selected population was 96%; the yield is not mentioned. These purities are not adequate for a large number of attractive applications, such as stem cell transplants, or the preparation of subpopulations for cell biology or immunology studies.

Most attempts to scale-up affinity cell separation procedures beyond laboratory scale have involved affinity columns packed with beads coated with antibodies, lectins, or staphylococcus protein A. Solutions containing cell mixtures flow through the column packing and, ideally, the ligands bind the specific cells of interest. In practice, however, a large fraction of the undesired cells bind nonspecifically in the columns such that the purity and yield of the selected cells is disappointingly low. For example, in a recently reported attempt to separate T lymphocytes from peripheral blood lymphocytes using soybean agglutinin-coated Sepharose beads in a column, Hertz et al. found that they could capture 90% of the T lymphocytes, but they also found 80% of the other lymphocytes were nonspecifically bound (Hertz et al. *Biotechnology and Bioengineering* 27:603–612, 1985). Procedures for cell purification employing the extremely high affinity of biotin and avidin have produced the best large-scale results using packed columns (Berenson et al. *J. Cell. Biochem.* 10D:239, 1986). Berenson et al. reported the concentration $2.5 \times 10^9$ target cells from 14% to 73% purity with a yield of 43%.

The most successful approach to large scale cell affinity separations has involved the use of magnetic particles. Magnetic particles have been used clinically to remove neuroblastoma or T cells from bone marrow transplants. 99.97% or more of the unwanted cells are removed from transplants initially containing over $10^{10}$ cells, but over half of the other cells are removed nonspecifically by the process (Vartdal et al. *J. Cell. Bioch.*, Sup. 10D: 252, 1986).

Because of the difficulties in implementing and scaling-up cell affinity separations, this promising technique has found very little practical application. There remains a need to be able to recover cells with higher yields and higher purities.

SUMMARY OF THE INVENTION

Many of these difficulties relating to yields and purities inherent in the processes of the prior art are overcome by the processes of this invention. A process for separating a target fraction of biological cells from a mixture of cells in a media by effecting contact between the cells in the mixture and a cell contacting surface having a ligand thereon with a specific affinity for the target cells and separating the contacting surface and the media is improved according to this invention by steps of effecting relative movement between the media mixture and the cell contacting surface to provide contact between the target cells and the contacting surface, forming an affinity bond between the cells and surface, while maintaining the shear force at the contacting surface at a value less than the developing bond strength between the target cells and the ligand on the contacting surface. The shear force divided by contact time squared preferably is maintained in the range of $2 \times 10^{-9}$ and 0.02 dynes/cm²/sec².

Alternatively, or in combination with such process, may be included the step of continuously renewing the cell contacting surface. In still another alternative process, or in combination with the above steps, there may be included the step of flowing the media mixture of cells to contact the cell contacting surface or vice versa at a nonsteady rate. Each of these processes, taken singly or in combination, increase the purity and yield of the separation.

The processes may include singly or in combination, the step of adjusting the area of the contacting surface to be less than 10 cm²/ml of media. Alternatively stated, the concentration of cell binding sites on the contacting surface is maintained to be less than ten times the concentration of target cells. This conserves ligand and reduces nonspecific binding. Each process or combination of processes may be used where the media is whole blood or diluted whole blood. These processes provide higher yields as well as higher purities of the desired cells than has been heretofore possible.

BRIEF DESCRIPTION OF THE DRAWING

The sole FIGURE is a representation of the cell collision rate with the contacting surface, plotted as the ordinant, versus shear force divided by contact time squared, plotted as the abscissa, for various affinity separation techniques.

DETAILED DESCRIPTION OF THE PREFERRED EMBODIMENT

The present invention provides processes for effecting efficient affinity cell separations for preparing high purity fractions of biological cells from mixtures of cells by contacting the cells with surfaces coated with immobilized ligands with specific affinity for the desired subpopulation of cells. These processes include both cell depletion processes in which a subset of cells is removed from the mixture of cells as well as positive selection processes in which there is prepared a specific subset from the mixture of cells. Cells, as the term is used herein, may include biological cells of any origin, including prokaryotic and eukaryotic organisms. By way of emphasis, noncellular particles including viruses, mycoplasma and particles in general can be purified using the affinity separation process of the invention.

An affinity cell separation process uses affinity cell separation devices with affinity contact surfaces. Cells which bind to the affinity contact surfaces, as desired, are referred to as the "target cells". The separation devices, as is known, may include bead columns, petri dishes, magnetic beads, fiber arrays, porous membranes, hollow fibers, roller bottles, emulsions, slurries, and the like. The affinity contact surfaces in the devices may be formed of any of the materials known to be useful for this purpose and include gels (such as polyacrylamide or agarose), polymers (such as polystyrene, polyacrolein, polyamines, polyarylates, polyesters, polyaramides, polyacrylonitriles, polysulfones, cellulosics, ionomers, and fluoropolymers), proteins, lipids, surfactants, glasses, and ceramics.

The surface of whatever device is selected, for example, the bottom of a polystyrene container, is coated with one member, the immobilized ligand, of a specific binding pair, i.e., ligand and receptor, where the receptors are on the subpopulations to be separated. The immobilized ligand has affinity for the cell subpopulation (the target cells) that is desired to be isolated and binds such subpopulation with specific affinity. The immobilized ligand may be, for example, an antibody molecule recognizing a specific antigen on the cell surface. The immobilized ligand could also be a specific ligand molecule, such as a lectin, dye, or a receptor substrate, that is bound by a receptor or ligand-binding molecule on the surface of the cell to be purified. The affinity ligand may also be, for example, biotin, avidin, protein A, an enzyme, an enzyme substrate, or a receptor. Sandwiches or combinations of ligands and ligand-binding molecules may be used. For example, T3-bearing cells may be captured by using a mouse monoclonal antibody specific for T3 and an immobilized antibody specific for mouse immunoglobulin, i.e., the mouse antibody. Molecular spacers or bridges may be used to facilitate interaction of the ligand and ligand-binding molecules.

The affinity ligands may be bound to the cell contacting surface by any of the well-known techniques. For example, physical adsorption, covalent chemistry, physical entrapment, hydrophobic interactions, or Van der Waals interactions may be used. Current techniques for the attachment of proteins to solid supports are reviewed in *Affinity Chromatography and Related Techniques*, edited by T. C. J. Gribnau, J. Vissen, and R. J. F. Nivand, Elsevier, 1982.

The cell mixture is placed in various media for transport, handling, etc. The media may be any suitable media that is not harmful to the cells, the ligand, or the ligand-binding molecule. Commonly used media include Hanks balanced salt solutions, RPMI 1640, phosphate buffered saline, Eagle's or Dulbeco's minimum essential media. Other common media and additives are described in *American Type Culture Collection Catalogue of Cell Lines and Hybridomas*, 5th edition, 1985, pp. 263-273 (American Type Culture Collection, Rockville, MD).

Cell affinity purification processes include, as noted above, depletion as well as positive selection processes. Such positive selection processes involve placing a mixture of cells, containing a desired subpopulation of cells to be separated, in a medium such that the cells contact the contacting surface and the desired cells become bound to the ligands thereon. The cells which do not become attached to the surface ligands are washed from the surface by additional media and discarded. Cells to be harvested which are bound or adhere to the affinity surface are removed by any well known method including scraping, agitating, fluid shear, use of an elution buffer, or by natural desorption.

(H. Wigzell, Scand. J. Immunology 5(55), pp. 23-30, 1976)

According to this invention the purities and yields of cell subsets obtained by many known affinity cell separation processes may be be improved even when operating on large volumes or high cell numbers. In the past, design and scale-up has been done largely by making empirical variations in procedures developed for other cell separation systems or by increasing the volumes and areas of processes which worked successfully at the bench scale. The frequent failure of such empirical approaches can be avoided by taking into consideration the following variables governing the interaction between the cell and the affinity contact surface: (1) the collision or contact rate, (2) the contact time, (3) the bond strength, (4) the shear force, and (5) the equilibrium binding constant.

According to the processes of this invention, optimal affinity surface areas are used along with techniques to greatly increase cell:affinity surface contact efficiency. Surface areas are selected by taking into account equilibrium binding constants. The contact efficiency is increased by both raising the collision rate and maintaining the shear force below certain limits determined by the contact time. The identification, measurement, and optimization of these key variables provides new affinity cell separation processes for separation of specific cells from flowing media, including whole blood, or under static conditions with much greater efficiency than previous procedures.

A particular affinity cell separation process requires a general definition of the properties of the separation process to be used for the application. This definition includes the purity and yield of the target cell that is required, the affinity ligand and affinity ligand immobilization technique, the starting cell mixture composition and its properties, biological or regulatory constraints, the affinity surface cell binding site density, equilibrium binding constant (or avidity) for binding of the cell to the affinity surface, and the bond strength for binding of the cell to the affinity surface.

Contact Rate

Next one must use a system which provides an adequate rate of contact between the cell and the affinity surface. Binding to the affinity surface cannot occur if the cell does not contact the affinity surface ligand. The rate at which cells contact the affinity surface is dominated by three processes: sedimentation, surface renewal, and interception. Diffusion rates for cells are negligibly small ($\leq 10^{-9}$ cm$^2$/sec) and may be ignored. Sedimentation refers to the settling of cells onto a surface due to gravitational or accelerative forces as provided by a centrifuge type device, for example.

Surface renewal is the process of removing the thin layer of media at the affinity surface and exchanging it with fresh media (containing cells) from the bulk solution. The repeated dipping of a support into a medium containing cells, then draining the medium from the surface, is an example of a surface renewal process. (G. Astarita, Mass Transfer with Chemical Reaction, Elsevier Publ. Co., 1967). Examples of known surface renewal devices include rotating cylinders partially filled with media flow inverters such as Kenics mixers, thin film contactors, and Taylor-Couette devices.

Interception is the process by which cells are impacted upon a surface by flow of the media. The forces required for efficient interception of cells are generally too high to permit binding of cells to the surface after steady state flow profiles have been established because the shear force exceeds the binding force for the binding of the cell to the affinity surface. However, according to this invention, high interception rates with low shear can be achieved using nonsteady flow, which includes pulsed or oscillatory flow or non-steady motion of the affinity support relative to the cells. When the flow or motion of the support through the media is steady, boundary layers or shear profiles develop which tend to prevent cells from actually contacting the surface. A description of this type of behavior may be found in M. Duszyk, J. Doroszewski, Progress in Surface Science, 15, pp. 369-399, 1984. Examples of nonsteady flow devices include pulsed flow through a conventional bead column or fiber array, or oscillatory motion of the affinity surface in the cell mixture.

Past affinity cell separation processes have relied on sedimentation. The collision rate or contact rate between the cell and the affinity surface (i.e., the cell:affinity surface collision rate) for sedimentation is the terminal settling velocity of the cells times the cell concentration times the affinity surface area projected onto a plane perpendicular to the direction of the accelerative force (usually just gravity).

The sedimentation terminal settling velocity can be calculated using Stokes Law:

$$V_t = \frac{2r^2 g(\rho_c - \rho)}{9\mu}, \quad (1)$$

where
$V_t$ = terminal settling velocity (cm/sec),
r = cell radius (cm),
g = gravitational acceleration (980 cm/sec$^2$),
$\rho_c$ = cell density (gm/cm$^3$),
$\rho$ = media density (gm/cm$^3$),
$\mu$ = media viscosity (gm/cm sec).

Thus, the sedimentation velocity for lymphocytes in aqueous media is about $4 \times 10^{-4}$ cm/sec. The cell:surface collision rate for $10^7$ cells/ml on the bottom of a petri dish is:

$$4 \times 10^{-4} \text{ cm/sec} \times 10^7 \frac{\text{cells}}{\text{cm}^3} = 4000 \text{ cells/sec cm}^2. \quad (2)$$

In some formats, the affinity surface is also settling. In such cases, the differential settling velocity is the important parameter. Magnetic beads as noted above have often been used for cell capture. The commonly used Dynal M450 beads settle faster than cells. The net sedimentation velocity or differential settling velocity is the difference between the measured bead velocity of $8 \times 10^{-4}$ cm/sec and the cell velocity, $4 \times 10^{-4}$ cm/sec. The net cell:surface collision rate is thus the same as equation (2) where the area is the area swept by the beads.

Also, according to this invention, surface renewal can increase the cell contact rate above that provided by sedimentation alone. The increased rate can be calculated from the rate at which surface is wetted and the cell concentration:

$$SR = \frac{A}{t} \times 2r \times C, \quad (3)$$

where

SR=cell contact rate due to surface renewal (cells/sec),
A/t=rate surface is wetted (cm²/sec),
r=cell radius (cm),
C=cell concentration (#/cm³).

The increased cell:surface contact rates due to interception and nonsteady flow can similarly be estimated using classical engineering calculations for two-phase flow (Bird et al., *Transport Phenomena*, John Wiley and Sons, NY, pp. 3-243, 1960). The cell:affinity surface contact rate can be increased manyfold by using devices which include both surface renewal and nonsteady flow phenomena.

A major reason for the relatively poor performance of previous affinity cell separation devices or processes is that they were designed to optimize diffusional mass transfer (e.g., maximizing surface area) rather than these more relevant contacting mechanisms. In Example 5, the use of a roller bottle (surface renewal approach) gives twice the collision rate of the best current procedure (magnetic particles in suspension; Kemshead et al., *Advances in Neuroblastoma Research*, Alan R. Liss, Inc. pp. 413-423, 1985) and 10 times the collision rate of the most common technique (sedimentation) when capturing cells from whole blood. The procedure used by Kemshead et al. gives about $8 \times 10^5$ collisions/second/ml which is the highest of all reports for which a collision rate can be estimated. Using surface renewal and non-steady flow procedures allows contact rate of $10^6$ to $10^9$ collision/sec/ml, far in excess of current procedures.

By proper consideration of the cell:surface contact rates and forces, the process of this invention has successfully removed 70% of the target cells from a sample of whole, undiluted human blood in one hour. The target cells were present at an initial concentration of $10^6$/ml which was 0.02% of the total blood cells. The captured cells were 95% viable and included less than 7% of the blood cells.

Shear Force

Further, according to this invention, shear forces on the cells bound to the affinity surface are maintained less than the developing bond strength between the cell and the affinity surface. The initial bond strength, following the initial contact between the cell and the affinity surface, is relatively low and cells may be removed by the shear forces caused by fluid flow. Most processes which produce high cell contact rates also produce high shear. The objective is, therefore, to maximize the contact efficiency of binding of the cells and the affinity surface by providing high contact rates while maintaining shear forces that do not exceed the binding force or bond strength securing the cell to the affinity surface.

According to this invention, use is made of the determination that the bond strength between the cell and affinity surface is a function of the contact time and may be described by the following equation:

$$\text{bond strength} = \text{rate factor} \times (\text{contact time})^2 \qquad (4)$$

The following units may be used with this equation: bond strength (dynes/cm²), rate factor (dynes/(cm² sec²)), contact time = $t_c$ (sec).

The rate factor in the above equation, which determines the rate at which the bond strength develops, is a function of the following variables: receptor density, stability, and mobility; temperature; ligand affinity, density, and mobility; ligand immobilization technique; media composition; and cell-mediated behavior such as receptor shedding. For example, for the binding of mouse T cells to immobilized 7D4 antibody (an IgM monoclonal antibody specific for an IL2 receptor subunit), the rate factor is determined to be $5.6 \times 10^{-6}$ dynes/(cm² sec²) at 4° C. and $1.4 \times 10^{-4}$ dynes/(cm² sec²) at 37° C., under the conditions described in Example 2.

The published literature contains many examples of affinity separations where there is essentially no shear and the cells are contacted via sedimentation alone (e.g., panning, magnetic beads). There are relatively few examples of processes which enhance the contact rate above sedimentation alone (e.g., fibers, bead or gel columns) and these have involved high shear rates. For example, current theory regarding the strength of cell-:ligand bonds led Hertz et al. op. cit. to operate their column at a flow rate where the shear force divided by the contact time squared was 7 orders of magnitude higher than the values used in Example 2 (below). Under such conditions, cells would bind only in a few isolated low flow rate regions of the column where the shear force is reduced and less than the bond strength.

FIG. 1 illustrates the relative operating characteristics of current methods and some of the improved methods described herein. Although the amount of shear tolerated by cells during initial binding is much lower than commonly believed, there are processes with low shear that can be used to obtain much higher cell contact rates and cell separation efficiencies than current methods. The shear force during contact must be kept below and about 0.02 dynes/cm² sec², which is the upper limit of observed bond strength rates.

The amount of nonspecific cell binding to the affinity surface can be greatly reduced by operating processes at the correct level of shear. Moving the media relative to the affinity surface such that the shear force is intermediate between the binding strength of cells attaching specifically and those which are bound nonspecifically reduces nonspecific binding significantly. Another attractive technique for reducing nonspecific binding is to allow cells to bind and develop a high bond strength with low shear, then to generate a high shear to dislodge and remove nonspecifically bound cells which do not develop as strong a bond strength as those cells which are specifically attached.

Affinity Surface Area

Cell separation processes can also be improved according to this invention by selecting the appropriate affinity surface area in the cell separation device. This selection is based on the equilibrium binding constant $K_{eq}$ (avidity) for the binding of the cells to the affinity surface:

$$K_{eq} = \frac{[\text{bound cells}]}{[\text{free cells}] \times [\text{free sites}]} \qquad (5)$$

Attempts to bind all the target cells in a mixture in one treatment are futile because of the equilibrium binding phenomenon. Once a large proportion of the cells have been bound, it takes a very large increase in affinity binding sites (or area) to bind more cells. However, using large affinity surface areas increases nonspecific binding proportionately. For example, if 10 cm² of affinity area bound 90% of the target cells with 2% nonspecific binding, then 100 cm² of the same affinity area would be needed to give 99% target cell binding and the nonspecific binding would be about 20%.

The equilibrium binding constant ranges from $10^{10}$ to $10^{18}$ M$^{-1}$ depending on the cell type, the affinity ligand, the medium, and the immobilization technique. The concentration of binding sites is proportional to the affinity surface area; the number of such sites has been measured and found to range up to $5 \times 10^6$ sites/cm$^2$. Though the actual concentration of binding sites chosen varies widely depending on the particular application, target cell, affinity ligand, and support, optimal values are generally less than 10 times the concentration of target cells in the media and preferably less than 2 times such concentration where concentration of binding sites is defined as the affinity area per unit volume times the number of binding sites per unit area. The optimum binding site concentration is calculated using the equilibrium binding equations for both target cells and nonspecifically bound cells. By setting the derivative of the ratio of specific to nonspecific binding with respect to binding site concentration equal to zero one can solve for the optimum binding site concentration:

$$K = \frac{[B]}{[T-B][S-B]} \quad (6)$$

where
B = Concentration of Bound Target Cells
T = concentration of Target Cells
K = Equilibrium binding constant for target cells
S = Binding site concentration.
Solving for B using the quadratic formula:

$$B^2 - (S + T + 1/K)B + TS = 0 \quad (7)$$

$$B = 1/2[(S + T + 1/K) - \sqrt{(S + T + 1/K)^2 - 4TS}]. \quad (8)$$

The ratio of specific to nonspecific cell binding can be written similarly:

$$\frac{B}{N} = \frac{1/2[S + T + 1/K) - \sqrt{(S + T + ^1K)^2 - 4TS}]}{1/2[(S + T_n + 1/K_n - \sqrt{(S + T_n + 1/K_n)^2 - 4TS}]} \quad (9)$$

where
N = concentration of cells bound nonspecifically
$T_n$ = concentration of all cells
$K_n$ = equilibrium binding constant for cells attaching independently of the ligand.
The optimal site concentration is calculated by setting the derivative of eqn(9) with respect to S equal to zero and solving for S.

With commonly used affinity site densities and target cell concentrations this corresponds to under 10 cm$^2$ of affinity area/ml media. This is less than is commonly used in the prior art.

The equilibrium nature of cell binding requires the use of relatively large affinity surface areas when essentially all of the target cells in the mixture are to be captured in one treatment. When very pure samples of a target cell subpopulation are desired and the yield of the cell type is a secondary concern, much less area is necessary or desirable since the amount of nonspecific cell binding is generally proportional to the surface area. In general, the area selected using the equilibrium constant is considerably less than is commonly practiced.

Using the processes described above to increase the cell:affinity surface contact rate, limit the shear force on the attaching cells, and select an appropriate affinity surface area results in superior affinity cell separations providing both high yields and/or higher purities of the target cells. The various processes may be used alone or in combination with each other as desired.

EXAMPLE 1

Attachment of Antibodies to a Culture Dish Surface

The following procedures were used to bind antibodies to the surface of a polystyrene culture dish or to the surface of a magnetic bead. Goat anti-rat IgM antibody (GαR IgM) (Cappel) was immobilized on polystyrene 35 mm tissue culture dishes at a concentration of 0.1 μg/cm$^2$ using the following procedure. A volume of 0.3 ml of a carbodiimide solution (0.05 g of carbodiimide hydrochloride per ml of 0.1M sodium acetate pH 4.8) and 0.3 ml containing 0.96 μg goat anti-rat IgM per ml of 0.1M sodium acetate pH 4.8 were added to each culture dish well. The dish was incubated with rocking for 60 minutes at 25° C. The wells were washed 3 times with 3 ml of PBS. A second or capture antibody was added in 3 ml of PBS at a concentration of 3 μg/ml to each dish. The dishes were again incubated at room temperature for 1 hour without mixing. Excess antibody was rinsed off with two 3 ml aliquots of PBS and one aliquot of PBS containing 1% heat inactivated fetal calf serum (FCS) (Gibco). The remaining protein binding sites on the plate were blocked or quenched by adding 0.1% bovine serum albumin (BSA) in 3 ml of PBS to the dish. The dish was then incubated for 30 minutes at room temperature without mixing. The dish was finally rinsed 3 times with aliquots of 3 ml PBS. In one case the second antibody was that designated 187.1, which is specific to mouse immunoglobulin, and was obtained from John McKearn (E. I. du Pont de Nemours and Company, Glenolden, PA). In another case, the second antibody was that designated 7D4, which is a rat IgM monoclonal antibody specific for a mouse IL-2 receptor subunit. 7D4 was obtained from Tom Waldman, NCI, Bethesda, MD.

Antibody molecules were also coupled to culture dishes by simple adsorption. For the physical adsorption coupling procedure, 3 ml of phosphate buffered saline (PBS) was added to the dish before addition of the first antibody The first antibody was allowed to absorb to the plate for an hour at room temperature before washing 3 times with 3 ml PBS. The first antibody was used to bind to the support a second antibody with specific affinity for the target cell (i.e. the affinity ligand). The second antibody can be used as a myeloma cell culture supernatant. The second antibody was added to 3 ml of PBS in the dishes and incubated statically for an hour at room temperature. The dishes are rinsed 2 times with PBS, once with PBS+1% FCS, and quenched with 0.1 ml bovine serum albumin (BSA) in PBS for 30 min. The dishes are rinsed 3 times with 3 ml PBS immediately before addition of cells.

EXAMPLE 2

Equilibrium Binding Constant Measurements

Equilibrium binding constant measurements were carried out in Corning 35 mm polystyrene tissue culture dishes. Antibodies, which were used as the affinity ligands, were immobilized on the culture dish surface using procedures described in Example 1. Prior to addition of cells to the affinity surface, the cells were collected by centrifugation for 10 min at 1000×g, decanted, and resuspended in PBS+1% FCS. A selected number of cells (usually 10⁶ or more per dish) were incubated in the dish for two hours at 37° C. Nonadherent cells are removed by decanting the media from the dish and rinsing the dish twice with 3 ml aliquots of PBS+1% FCS which were gently added and removed with a pipet. Adherent cells were removed by scraping the dish with a PVC scraper and rinsing 2 times with PBS+1% FCS. The cells were counted on a Coulter Counter with a 50 micron aperture.

For equilibrium experiments, the controls for the specificity of cell binding consisted of dishes which had undergone the same processing but did not receive the second antibody specific for the target cell to be captured. Other controls for cell binding specificity that were tested included dishes with no first antibody and dishes with a second, irrelevant antibody not specific for the target cell. Controls were run during every experiment for every variable. Some of the more important sources of variation in the efficiency of cell binding were found to include the age, health, and activity of the cells; the second antibody coupling efficiency; and the procedure for flushing nonadherent cells from the dishes.

The total cells captured per unit area by the affinity surface as a function of the amount (density) of antibody initially applied to the plates was determined for CTLL cells (American Type Culture Collection #P1B-162) captured by 7D4 antibody which has been physically absorbed to goat-α-rat IgM. The goat-α-rat IgM antibody was covalently linked to the plate by the carbodiimide compling procedure (Example 1). The total number of cells captured was found to reach a maximum and to decline at very high levels of 7D4.

The binding of cells as a function of cell concentration was determined. These experiments were made using an optimal level of 7D4 antibody (1.0 μg/cm²). The equilibrium binding constant $(K_{eq})$ is defined as $K_{eq} = \dfrac{[B]}{[T-B][S-B]}$ where,
B = specifically bound cells,
T = total cells,
S = total sites,
and the brackets denote concentration.

The equilibrium constant and site density were determined from the binding data using nonlinear regression methods. The site densities and equilibrium binding constants for several representative cell and affinity surface systems are summarized in Table I.

There are several important points to notice in the data presented in Table I. Covalent immobilization of the first antibody gives much different values than does physical adsorption. Physical adsorption gives site densities equivalent to 5 monolayers of cells with 7D4. Direct covalent binding of 7D4 and covalent binding of the first antibody (GαR IgM), followed by physical adsorption of 7D4, gives comparable results. A dramatic effect of FCS in the media is noted. The similarity in values obtained with different surfaces (polystyrene culture dishes vs magnetic particles) is noted.

The magnitudes of the equilibrium binding constants reported in Table I are very high. Literature values for the equilibrium binding constants of monoclonal antibodies for their antigens in free solution range from about $10^6$ to $10^{10}$ M$^{-1}$. The site density is here defined as the maximum number of cells which can bind to the surface. The very high equilibrium binding constants determined for the binding of cells to an antibody-coated affinity surface arises from the fact that many antibody binding sites are occupied by a single cell and many bonds are thereby formed between the affinity surface and an individual cell.

The fundamental reason for the high affinity or avidity of the cell for the affinity surface is the formation of multiple bonds between the cells and the surface which drastically reduces the cell desorption rate.

TABLE I

EXPERIMENTALLY MEASURED EQUILIBRIUM CONSTANTS AND SITE DENSITIES FOR VARIOUS CELL AND AFFINITY SURFACE COMBINATIONS

| First Antibody | Second Antibody | Cell | Equilibrium Constant ($10^{15}$M$^{-1}$ ± 95% C.L.) | Site Density ($10^6$/cm² ± 95% C.L.) |
|---|---|---|---|---|
| | ads α-THY | CTLL | 1.85 ± 12% | 0.435 ± 2% |
| | 1.2 ads GαR IgG | Mouse Hybridoma producing rat IgM | 1.64 ± 47% | 0.032 ± 16% |
| | carb 7G7 | HUT | 0.99 ± 7% | 0.785 ± 2% |
| ads GαR IgG | PS1/30 | CTLL | 0.79 ± 9% | 0.354 ± 2% |
| ads GαR IgM | 7D4 | CTLL | 0.017 ± 9% | 5.91 ± 7% |
| | carb 7D4 | CTLL | 1.35 ± 15% | 0.323 ± 3% |
| carb GαR IgM | 7D4 | CTLL | 2.35 ± 2% | 0.183 ± 1% |
| carb GαR IgM | 7D4-mag. beads | CTLL w/15% FCS media | 1.45 ± 20% | 0.519 ± 6% |
| carb GαR IgM | 7D4 | CTLL w/15% FCS media | 0.54 ± 18% | 1.25 ± 5% |
| carb GαR IgM F(AB')₂ | 7D4 | CTLL | 1.49 ± 7% | 0.29 ± 1% |

Note: A monolayer of cells is approx. 10⁶/cm².
*ads = adsorbed
*carb = carbodiimide Because cell binding, as demonstrated above, is reversible, it is not possible to bind all of the target cells. Thus, attempts to increase the affinity surface area in order to bind all of the target cells will reach the point of diminishing returns where nonspecific binding will increase faster than the specific binding of target cells to the affinity surface.

EXAMPLE 3

Affinity Surface Area

Goat anti-mouse IgG antibody (Jackson Immunoresearch) was immobilized on a polystyrene tissue culture plate, as described in Example 1. The second antibody affinity ligand, a monoclonal antibody designated GL439, specific for a human IL2 receptor subunit (Tac) was bound to the surface coated with goat anti-mouse IgG at a concentration of 1.0 $\mu g/cm^2$. $10^7$ HUT 102 human cells (ATCC #P1B-162) were added to the different affinity surface areas. The specific and nonspecific cell binding were as follows:

| $cm^2/10^7$ cells* | % specific binding | % nonspecific** |
|---|---|---|
| 2.5 | 7.5 | 0.6 |
| 5.0 | 17 | 1.3 |
| 30 | 84 | 5.4 |
| 100 | 86 | 25 |
| 450 | 91 | 40 |

*Affinity surface area/$10^7$ cells.
**Binding to surface prepared using same process as that for affinity surface, except second antibody was not included.

EXAMPLE 4

Affinity Isolation of Target Cells from Whole Blood

Capturing cells from whole blood is a particularly difficult task because of the high cell density (3 to $5 \times 10^9$/ml) and the high viscosity of blood which drastically reduces the cell contact efficiency at a given shear level. $2 \times 10^6$ mouse CTLL cells were added to 2 ml whole human blood (heparinized) at 4° C. Magnetic beads (Dynal ME-450) coated with 7D4, an IgM monoclonal antibody against a mouse IL-2 receptor subunit (TAC), were suspended in the blood at a concentration of $4 \times 10^7$/ml. This concentration of beads is calculated to give a contact rate of $7.5 \times 10^6$ collisions/sec/ml which is enough to insure that 99% of the CTLL cells are contacted at least once during the two hour incubation. Other published protocols (although no previous report has cited application to whole blood) use contact rates orders of magnitude less than this (Kemshead, et al., *Adv. in Neuroblastoma Res.*, pp. 413–423. Alan R. Liss, 1985). After two hours, the beads and adherent cells were captured using a magnet, the nonadherent cells were poured off, and the beads were washed by resuspending in 1 ml of PBS, recapturing with a magnet, and pouring off the PBS three times. CTLL cells were detected in the mixtures by staining with fluorescein-labelled anti-THY 1.2, a rat IgG monoclonal antibody specific for the T cell marker THY 1.2 (Becton Dickinson), and analyzing on a flow cytometer. The initial concentration of CTLL cells was 0.03%; the final concentration ranged from 6 to 63% with a yield of 13 to 48%. The shear force on a cell at the surface of a bead was about $1.6 \times 10^{-11}$ dynes/$cm^2$, and the contact time was about 0.4 minutes. Under these conditions, the shear force, F, divided by the square of the contact time, $t_c$, is about $10^{-10}$ dynes/$cm^2$/$min^2$.

EXAMPLE 5

Use of Surface Renewal to Increase Cell and Affinity Surface Contact Efficiency Goat anti-mouse IgG antibody (Jackson Immunoresearch) was immobilized on a 70 $cm^2$ sector of a Corning 490 $cm^2$ tissue culture roller bottle. A monoclonal antibody, designated 7G7, specific for a human IL2 receptor subunit (TAC) was bound to the surface coated goat anti-mouse IgG at a concentration of 0.08 $\mu g/cm^2$. $10^7$ HUT 102 human cells (ATCC #P1B-162) were added to 7 ml whole human blood. The bottles were rolled at 1 rpm for 1 hour at 26° C. The cell:surface contact rate was about $3 \times 10^6$ collisions/(sec ml), the shear force on the cells at the surface was 0.4 dynes/$cm^2$, the average contact time per collision was 10.8 seconds. Based upon the equilibrium constant of $10^{15} M^{-1}$ (liters/mole cells), the maximum cell site density of $7.9 \times 10^5$/$cm^2$, and the available area of 70 $cm^2$, the predicted cell capture at equilibrium would be 92%.

The adherent and nonadherent cells were analyzed on a flow cytometer by staining the HUT cells with 7G7 and then FITC-labelled goat-anti-mouse (Tago). Thirty-four percent of the HUT cells were captured along with only 0.6% of the blood cells. Under these conditions, the shear force, F, divided by the square of the contact time, $t_c$, is 12.3 dynes/$cm^2$/$min^2$.

Under static conditions (sedimentation only) the collision rate is 1/12 of the above rate and the binding of HUT cells from whole blood is not distinguishable above background (1%).

EXAMPLE 6

Use of Nonsteady Flow to Improve Cell Affinity Separation Processes

The use of nonsteady flow has several advantages for cell affinity capture processes. Nonsteady flow enhances the collision efficiency by disrupting flow boundary layers. With proper selection of flow rates, nonsteady flow processes provide at different times both reduced shear forces that enhance binding efficiency during cell contact, and increased shear forces to reduce the level of nonspecific cell binding.

A Corning tissue culture roller bottle (490 $cm^2$) was coated with goat anti-rat IgM first antibody and then 7D4, an IgM antibody against murine IL2 receptors. $8 \times 10^6$ CTLL cells in 20 ml Iscove's media with 15% calf serum were added to the bottle and incubated statically for 4 minutes at 22° C. The bottle was rolled at 5 rpm for one minute and then stopped for 4 additional minutes. After 6 such cycles (30 minutes) cell binding was 57% while nonspecific binding was only 4%. Cells and bottles prepared identically but rolled steadily at 1 rpm bound only 30% of the cells with 12% nonspecific binding. Under the experimental conditions, the cell binding site density was $7.9 \times 10^5$/$cm^2$, the equilibrium binding constant is $0.99 \times 10^{15}$ liters/mole cells, the average collision rate in each experiment was about 200 collisions/(sec $cm^2$), the shear force while turning at 1 rpm was about 0.02 dynes/$cm^2$ and about 0.12 dynes/$cm^2$ at 5 rpm. Under these conditions, equilibrium binding is/was 77% of the total cells added. The average contact time at 1 rpm was 10.8 sec, the contact time at 5 rpm was 2.2 sec, the average contact time during the static intervals was 2 minutes. The shear force divided by the contact time squared at 1 rpm was 0.617 (dynes/cm$^2$/min$^2$), at 5 rpm was 89 (dynes/cm$^2$/min$^2$), and statically was 0.

We claim:

1. In a process for separating a target fraction of biological cells from a mixture of cells in a media by effecting contact between the cells in the mixture and a cell contacting surface having a ligand thereon with a specific affinity for the target cells and separating the contacting surface and the media, wherein the improvement comprises the steps of:

effecting relative movement between the media mixture of cells and the cell contacting surface at a nonsteady rate, thereby providing contact for a period of time between the cells and the contacting surface and increase the purity and yield of the separation; and maintaining a shear force at the contacting surface to a value less than developing bond strength between the target cells and the ligand.

2. The process set forth in claim 1 wherein the shear force divided by the square of the contact time is adjusted to between $2\times10^{-9}$ and 0.02 dynes/cm$^2$ sec$^2$.

3. The process set forth in claim 1 wherein the shear force is adjusted to be less than the developing bond strength between the target cells and the contacting surface, said bond strength being proportional to the product of a rate factor and the square of the contact time.

4. The process set forth in claim 3 wherein the rate factor is adjusted by changing a variable selected from the group consisting of receptor density, receptor stability, receptor mobility, temperature, ligand affinity, ligand density, ligand mobility, ligand immobilization technique, media composition and cell-mediated behavior.

5. The process set forth in claim 4 wherein the cell contacting surface is provided by devices which permit cell contact at shear forces divided by the square of the contact time is between $2\times10^{-9}$ and 0.02 dynes/cm$^2$/sec$^2$ and includes the step of adjusting the area of the contacting surface to be less than 10 cm$^2$/ml of media.

6. The process set forth in claim 5 wherein the media is whole blood.

7. The process set forth in claim 1, which further includes adjusting media flow rate to obtain a target cell to contacting surface contact rate greater than that created by the inherent differential sedimentation velocity of the target cells and the contact surface.

8. The process set forth in claim 1, which further includes the step of adjusting the area of the contacting surface to be less than 10 cm$^2$/ml of media.

9. In a process for separating a target fraction of biological cells from a mixture of cells in a media by effecting contact between the cells in the mixture and a cell contacting surface having a ligand thereon with a specific affinity for the target cells and separating the contacting surface and the media, wherein the improvement comprises the steps of:

effecting relative movement between the media mixture and the cell contacting surface for a contact time sufficient to attach the target cells to the contacting surface by an affinity bond between the cells and the surface; and maintaining a shear force at the contacting surface at a value less than developing bond strength between the target cells and the ligand.

10. The process set forth in claim 9 wherein the shear force divided by the square of the contact time is adjusted between $2\times10^{-9}$ and 0.02 dynes/cm$^2$/sec$^2$.

11. The process set forth in claim 9 or 10 which further includes the step of continuously renewing the cell contact surface with media containing the mixture of cells.

12. The process set forth in claim 10, which further includes the step of using one of a group consisting of rotating cylinders, flow inverters, thin film contactors, and Taylor-Couette devices to effect such surface renewal.

13. The process set forth in claim 10, which further includes the step of flowing the media mixture of cells against the cell contacting surface at a nonsteady flow rate, to increase the purity and yield of the separation.

14. The process set forth in claim 13, which further includes the step of adjusting the area of the contacting surface to be less than 10 cm$^2$/ml of media.

15. The process set forth in claim 9, which further includes adjusting media flow rate to obtain a target cell to contacting surface rate greater than that created by the differential sedimentation velocity of the target cells and the contact surface.

16. The process set forth in claim 15 wherein the shear force divided by the square of the contact time is adjusted between $2\times10^{-9}$ and 0.02 dynes/cm$^2$/sec$^2$.

17. The process set forth in claim 9, which further includes maintaining the shear force at the contacting surface at a value intermediate of the developing bond strengths of the target cells and other cells that may be non-specifically bound to the contacting surface, to preferentially remove the non-specifically bound cells.

18. The process set forth in claim 9 wherein the shear force is increased at the end of the cell contacting process to preferentially remove non-specifically bound cells from the contacting surface.

19. The process set forth in claim 9 wherein the shear force is increased at the end of the cell contacting process to preferentially remove from the contacting surface cells of the media mixture that may be nonspecifically bound thereto.

20. The process set forth in claim 9 wherein the media is whole blood.

21. The process set forth in claim 20 wherein the media is diluted.

22. In a process for separating a target fraction of biological cells from a mixture of cells in a media by effecting contact between the cells in the mixture and a cell contacting surface having a ligand thereon with a specific affinity for the target cells and separating the contacting surface and the media, wherein the improvement comprises the steps of:

flowing the media mixture to contact the cell contacting surface to attach the target cells to the contacting surface by an affinity bond between the cells and surface; and maintaining the contact rate between the mixture cells and the contacting surface between 10$^6$ and 10$^9$ collisions/second/ml.

23. The process set forth in claim 22, which further includes the step of:

maintaining a shear force at the contacting surface at a value less than the developing bond strength between the target cells and the ligand.

24. The process set forth in claim 23, which further includes the step of continuously renewing the cell contacting surface with media containing the mixture of cells.

25. The process set forth in claim 24 wherein the media is whole blood.

26. In a process for separating a target fraction of biological cells from a mixture of cells in a media by effecting contact between the cells in the mixture and a cell contacting surface having a ligand thereon with a specific affinity for the target cells thereby providing specific binding sites for the target cells, but some of the cells in the mixture becoming non-specifically bound to the binding sites, and separating the contacting surface and the media, the improvement comprising the steps of:
  adjusting the surface area of the contacting surface to provide a concentration of cell binding sites which is less than 10 times the concentration of target cells in the media;
  maintaining a shear force at the contacting surface at a value less than the developing bond strength between the target cells and the ligand; and
  continuously renewing the cell contacting surface with media containing the cell mixture.

27. The process of claim 26, which further includes the step of:
  effecting non-steady movement between the cells and the surface.

28. The process set forth in claim 27 wherein the media is whole blood.

29. The process set forth in claim 26, which further includes adjusting media flow rate to obtain a target cell to contacting surface contact rate greater than that created by the inherent differential sedimentation velocity of the target cells and the contact surface.

30. In a process for separating a target fraction of biological cells from a mixture of cells in a media by effecting contact between the cells in the mixture and a cell contacting surface having a ligand thereon with a specific affinity for the target cells thereby providing specific binding sites for the target cells, but some of the cells in the mixture becoming non-specifically bound to the binding sites, and separating the contacting surface and the media, wherein the improvement comprises the step of:
  adjusting the concentration of binding sites to a value less than or equal to the value calculated by setting the derivative with respect to S of the ratio of specific (B) to non-specific (N) cell binding equal to zero, where the ratio is defined by:

$$\frac{B}{N} = \frac{S + T + 1/K - ([S + T + 1/K]^2 - 4TS)^{\frac{1}{2}}}{S + T_n + 1/K_n - ([S = T_n + 1/K_n)^2 - 4T_nS)^{\frac{1}{2}}}$$

where S is the cell binding site concentration, T is the concentration of target cells, K is the equilibrium binding constant of the target cells and binding sites, $T_n$ is the concentration of cells in the media, and $K_n$ is equilibrium binding constant for cells non-specifically bound to the contacting surface;
  maintaining a shear force at the contacting surface at a value less than the developing bond strength between the target cells and the ligand; and
  effecting relative movement between the media mixture of cells and the cell contacting surface at a nonsteady rate, thereby to provide a contact for a period of time between the cells and the contacting surface and increase the purity and yield of the separation.

31. The process set forth in claim 30, which further includes the step of adjusting the area of the contacting surface to be less than 10 cm$^2$/ml of media.

* * * * *

UNITED STATES PATENT AND TRADEMARK OFFICE
CERTIFICATE OF CORRECTION

PATENT NO. : 5,215,926
DATED : June 1, 1993
INVENTOR(S) : Arthur W. Etchells, III; and Dale R. Peterson It is certified that error appears in the above-indentified patent and that said Letters Patent is hereby corrected as shown below:

In column 18, claim 30, line 30, please delete the "a" in between "thereby to provide" and "contact for".

Signed and Sealed this

Seventh Day of February, 1995

Attest:

BRUCE LEHMAN

Attesting Officer

Commissioner of Patents and Trademarks